United States Patent [19]
Antonucci et al.

[11] Patent Number: 5,508,342
[45] Date of Patent: Apr. 16, 1996

[54] POLYMERIC AMORPHOUS CALCIUM PHOSPHATE COMPOSITIONS

[75] Inventors: Joseph M. Antonucci, Kensington; Edward D. Eanes, Annapolis; Drago Skrtic, Gaithersburg, all of Md.

[73] Assignee: The United States of America as represented by the Secretary of Commerce, Washington, D.C.

[21] Appl. No.: 189,708

[22] Filed: Feb. 1, 1994

[51] Int. Cl.$^6$ .............. C08K 3/32; C08K 3/10; A61K 6/033
[52] U.S. Cl. .......... 524/788; 523/115; 523/116; 523/118; 524/417; 524/436
[58] Field of Search ............ 523/115, 116, 523/118; 524/417, 788, 436

[56] References Cited

U.S. PATENT DOCUMENTS

| | | | |
|---|---|---|---|
| 3,655,605 | 4/1972 | Smith | 523/116 |
| 3,751,391 | 8/1973 | Smith | 523/116 |
| 4,288,355 | 9/1981 | Anderson et al. | 523/116 |
| 4,373,217 | 2/1983 | Draenert | 523/115 |
| 4,380,432 | 4/1983 | Orlowski et al. | 523/118 |
| 4,668,712 | 5/1987 | Hino et al. | 523/116 |
| 4,886,843 | 12/1989 | Walton | 523/116 |
| 4,918,136 | 4/1990 | Kawaguchi et al. | 523/116 |
| 5,276,068 | 1/1994 | Waknine | 523/116 |
| 5,321,053 | 6/1994 | Hino et al. | 523/116 |

*Primary Examiner*—Peter A. Szekely
*Attorney, Agent, or Firm*—Leydig, Voit & Mayer, Ltd.

[57] ABSTRACT

A mineralizing composition for skeletal tissue comprising a mixture of an unsaturated monomer system, and a particulate mineralizing agent.

23 Claims, 5 Drawing Sheets

POLYMERIC AMORPHOUS CALCIUM PHOSPHATE COMPOSITIONS

BACKGROUND OF THE INVENTION

1. Technical Field

The present invention relates to a new type of bioactive composition which can be used in a prophylactic or reconstructive manner by preserving substantially sound mineralized tissue as well as for promoting remineralization of minerally defective skeletal tissue, such as teeth and bones. More particularly, the present invention is directed to compositions containing amorphous calcium phosphate and unsaturated monomers and to the hardened polymeric composites which they form. The present invention is also directed to a method of treating teeth and bones to effect mineralization.

2. Discussion of Related Art

Over the years, various materials have been used to treat, fill or alter skeletal tissue or to adhere a prosthetic device thereto. Thus, in the fields of orthopedics and dentistry, materials have been used and sought which seal or fill cracks or caries in bones or teeth and which provide support, strength and resistance to deterioration due to the environment found in the particular portion of the body in which they are used. Such materials have included various kinds of metals including alloys and amalgams, inorganic compositions, including ceramic materials, as well as plastic materials, including organic polymers. While many of these materials have been fairly effective in providing several of the desirable properties such as affinity for living tissue, for example skeletal tissue, and possibly foreign materials; mechanical strength; inertness to the biological environment in which they are placed; storage stability; and ease of manipulation, many lack one or more of these desirable properties. In addition, some of these materials cause damage to adjacent tissue, by erosion or the like, at or subsequent to the time when they are introduced to the body or demonstrate unacceptable levels of toxicity.

It has been realized that those materials which are closest to skeletal tissue both chemically and structurally, are least likely to demonstrate the aforementioned problems. Furthermore, where the materials are sufficiently similar in structure and chemical properties to the skeletal tissue, the body perceives little difference in chemical characteristics, performance or function at the affected site.

The high concentrations of inorganic substances distinguish skeletal tissue such as teeth and bones, from other types of tissue. In vertebrates, skeletal tissue is characterized by high concentrations of calcium and phosphate ions with lower proportions of sodium, magnesium, carbonate and fluoride ions. Characteristics of hardness and rigidity are attributable in skeletal tissue to these inorganic components, largely formed as crystalline salts. Although the mineral-material found in skeletal tissue as well as the chemical pathway to its formation appears to be complex, the predominant chemical structure most closely resembles that of the geomineral, hydroxyapatite (HAP), frequently also referred to as apatite. Although the mechanism by which HAP is formed in biological systems is still not fully understood, it is generally considered to have the formula $Ca_5OH(PO_4)_3$.

In the field of dentistry, a number-of inorganic and organic materials have been used over the years to adhere prosthetic devices to existing teeth. One such material which combines both organic and inorganic substances with the object of providing compatibility with living tissue, good adhesive properties and high compressive strength, has been described by Adachi (U.S. Pat. No. 4,684,673). The composition which is reported to provide these properties includes amorphous tricalcium phosphate, water and a water-soluble poly(carboxylic acid). After mixing, the amorphous tricalcium phosphate reacts with the carboxylic acid groups in the polymer to set. Such a composition, while somewhat useful not only as a cement but also as a filling material for defective bones and teeth, as well as being useful as a root canal filling material, appears to require a long setting time. Furthermore, as indicated above, while amorphous calcium phosphate can be used in a mineralizing treatment (also referred to as a "remineralizing" treatment when used in reconstruction at sites where skeletal tissue has been eroded), achieving the desired result is somewhat ineffective since a portion of the calcium ions originally present as calcium phosphate are depleted in the reaction with the carboxylic acid groups.

Tung (U.S. Pat. No. 5,037,639) describes a method and composition for mineralizing teeth, particularly to prevent and/or repair dental deficiencies such as dental caries, exposed roots and dentin sensitivity. The method employs amorphous calcium phosphate (ACP), amorphous calcium phosphate fluoride (ACPF) and amorphous calcium carbonate phosphate (ACCP). ACP, which appears to lack crystalline features, has an apparent compositional formula of $Ca_3(PO_4)_{1.87}(HPO_4)_{0.2}$ and exhibits a stoichiometry between that of dicalcium hydrogen phosphate and tricalcium phosphate. In the remineralizing process described, the method involves a short application of the aforementioned amorphous compounds or solutions thereof by contacting the dental tissue with a carrier, such as a solution, gel, chewing gum or toothpaste containing a mineralizing agent. While such compositions include materials suitable for mineralization, in applications involving solutions, either purely aqueous or where the carrier includes or is in the environment of water, such as in the gel, gum or toothpaste, temperature and, more importantly, pH, must be carefully controlled. In addition, since in most instances the duration of the treatment and contact by the mineralization site with the mineralizing composition is so brief, the procedure needs to be repeated several times. In addition, for certain types of treatment, by their nature, require the treatment to be performed by a dentist or dental technician. Furthermore, as with other crystalline materials, greater mechanical strength is provided by larger crystals. Slow growth over a long and continuous period of time favors larger crystal size, a characteristic of which is increased strength. Hence, while such a mineralization method achieves some of the objects of reducing the need for filling of teeth and providing mineralization compositions and methods, the short term direct applications of such compositions to the teeth do not favor the higher degree of strength and structure identified with HAP that occurs naturally in skeletal tissue.

SUMMARY OF THE INVENTION

The present invention is directed to bioactive compositions and to the solid composites which are formed therefrom. The composites are able to provide sufficient sustained and timed release levels of Ca and $PO_4$ ions which can provide long term protection against demineralization and promote mineralization of contiguous skeletal tissue. Accordingly, such composites are expected to have wide application as prophylactic, adhesive, prosthetic and restorative materials, particularly in the field of dentistry.

As used herein, in discussions of the present invention, terms such as "mineralizing", "mineralization" "remineralizing", "remineralization", and like terms have the meaning of forming solid inorganic structures which are chemically and structurally similar to naturally occurring skeletal tissue mineral. In particular, this involves the bioformation of HAP and similar naturally occurring substances from ACP. Skeletal tissue is generally defined as the bony, ligamentous, fibrous, and cartilaginous tissue forming the skeleton and its attachments. As used herein, the term is largely intended to refer to bones and teeth.

Also as used herein, the term "composite" is intended to mean not only a restorative material which employs a continuous polymeric matrix and a dispersed reinforcing filler or mineralizing agent, but also sealants, adhesives and cements containing the same filler. In contrast, the materials used to make the composites of the present invention are referred to as "compositions". The distinction is that the compositions of the present invention, while including the same filler, contain a "monomer system" rather than the "polymeric matrix" of the composite, the latter being formed from the monomer system of the composition by polymerization. The term "$PO_4$" is used to denote the total phosphate in solution or solid, i.e., the sum of all ionic phosphate species ($H_2PO_4^{-1}$, $HPO_4^{-2}$, $PO_4$). Analytic methods described herein measure only total phosphate ($PO_4$).

The composites and compositions of this invention incorporate as the filler an inorganic powder or particulate mineralizing agent with the monomer system or within a cross-linked polymeric matrix. The preferred inorganic particulate mineralizing agent is ACP. The cross-linked polymeric matrix is formed from a monomer system that includes unsaturated monomers, preferably including methacrylate moieties. A preferred monomer system is so selected as to provide a polymeric matrix, preferably cross-linked, of sufficient water permeability or hydrophilicity as to allow diffusion of water and ions into, through and out of the matrix and to the skeletal tissue surface with which the composite forms an interface. Thus, because of the relatively high solubility of ACP in aqueous solutions, high concentrations of calcium and phosphate ions are available for mineralization. Unlike the cements of Adachi, since the calcium ions in the present invention do not form salts with carboxylic acid moieties in a polymer, they exist in solution in ratios to phosphate ions which are favorable for the formation of HAP. Since a polymeric matrix is selected which provides a substantially permanent structure, strength and sufficient permeability for water and ions, timed release of calcium and phosphate ions from the mineralizing agent ACP occurs which promotes slow growth of larger HAP crystals at the polymeric matrix/skeletal tissue interface and in the body of the skeletal tissue. As used herein, the term "timed release" refers to the diffusion of ions over a protracted period of time through the polymeric matrix as well as the migration of the ions from the surfaces of the polymeric matrix to the surface and interior of the skeletal tissue or previously deposited HAP. The diffusion and migration processes occur simultaneously in the mineralization phenomenon. Finally, while the mineralization process occurs, sufficient strength is provided to the tooth or bone structure or to retain a prosthetic device immobilized on the bone or tooth by the mechanical strength of the composite, restorative or adhesive afforded by the polymeric matrix.

The mineralizing composite of the present invention is formed by a mineralizing composition which includes an unsaturated monomer system and an inorganic particulate or powder mineralizing agent. As indicated above, the mineralizing agent is preferably ACP and the unsaturated monomer system includes at least one monomer and preferably also includes at least one cross-linking agent. The unsaturated monomer system preferably includes a methacrylate moiety and a free-radical initiator. The latter is preferably a photoinitiator which induces polymerization by exposure to light of an appropriate wavelength. The monomer system may also include a polymerization accelerator.

The particulate inorganic mineralizing agent may also include a stabilizer which promotes mineralization at a suitable rate at the bone or tooth surface. Preferred materials include charged organic or inorganic species.

The present invention is also directed to a method of treating and mineralizing skeletal tissue. The method may also concomitantly or alternatively be used to adhere a prosthetic device to a bone or tooth or achieve partial restoration of skeletal tissue. The method involves contacting the portion of the skeletal tissue to be treated with a mineralizing composition that includes a mixture of an unsaturated monomer system and a particulate mineralizing agent and thereafter curing the composition.

When using the mineralizing compositions of the present invention in the treating and mineralizing method of the present invention, high, sustainable and timed release levels of calcium and phosphate ions are released from the matrix to precipitate as HAP crystals, such as those found in bone and tooth tissue. When stabilizers are employed in the compositions, ions released from the polymeric matrix show little tendency to reprecipitate on or within the matrix itself. Thus, most of the released ions are available for tooth or bone mineralization. The extended timed-release characteristics of the present invention are particularly advantageous in long-term sealant, adhesive and restorative uses, where prevention of tooth demineralization (e.g., in orthodontically treated teeth) or promotion of remineralization (e.g., in white spots, carious lesions, root caries, etc. ) is desirable. This obviates frequent reapplications of compounds such as is necessary with toothpastes, rinses and gel coatings used in remineralization treatments known heretofore.

Figure 6A:
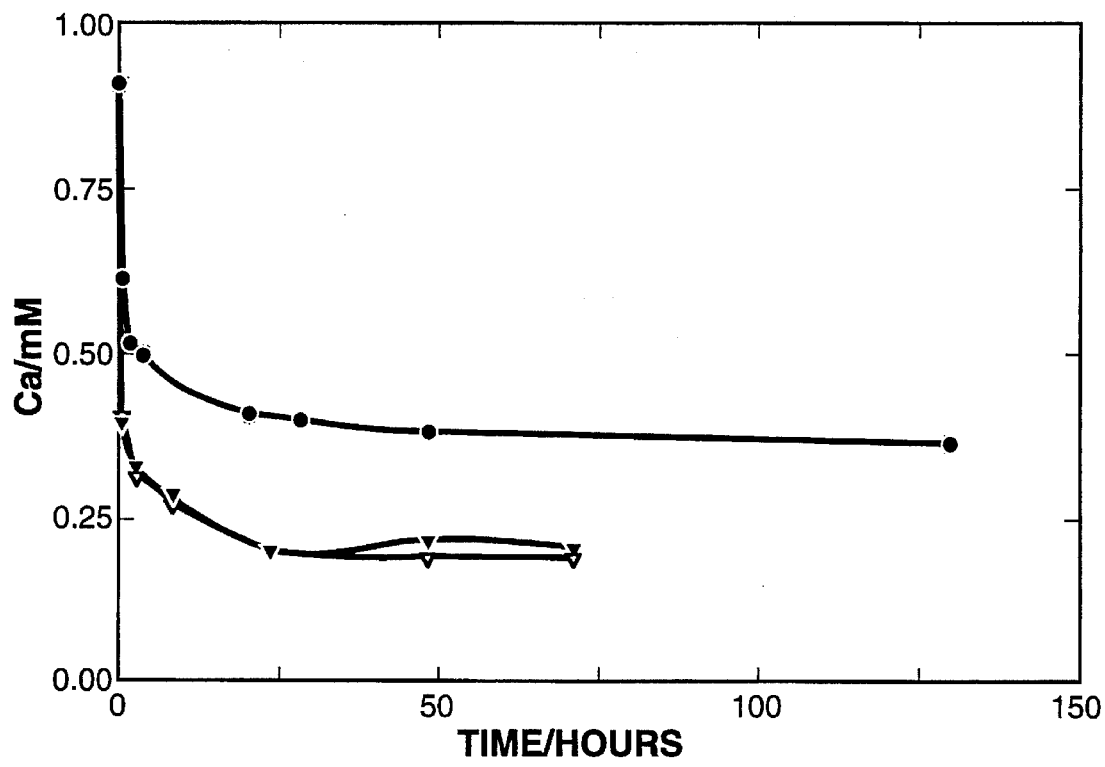

FIG. 6A shows graphically changes in $Ca^{2+}$ concentrations upon seeding (with 0.7 mg/mL HAP) ph 7.4 buffered solutions in which $P_2O_7$-ACP/resin IV disks had been immersed for 400 hours. At the time of seeding, the solutions contained 0.90 mmol/L $Ca^{2+}$ and 0.45 mmol/L total $PO_4$. (v) disk kept in solution after seeding, (v) disk removed before seeding (●) control solution prepared from $Ca(NO_3)_2$ and $Na_2HPO_4$ and not exposed to a disk but seeded with the same amount of HAP.

FIG. 6A shows graphically changes in total $PO_4$ concentrations upon seeding (with 0.7 mg/mL HAP) pH 7.4 buffered solutions in which $P_2O_7$-ACP/resin IV disks had been immersed for 400 hours. At the time of seeding, the solutions contained 0.90 mmol/L $Ca^{2+}$ and 0.45 mmol/L total $PO_4$. (v) disk kept in solution after seeding, (v) disk removed before seeding (●) control solution prepared from $Ca(NO_3)_2$ and $Na_2HPO_4$ and not exposed to a disk but seeded with the same amount of HAP.

Figures 7A, 7B, 7C, 7D, 7E:
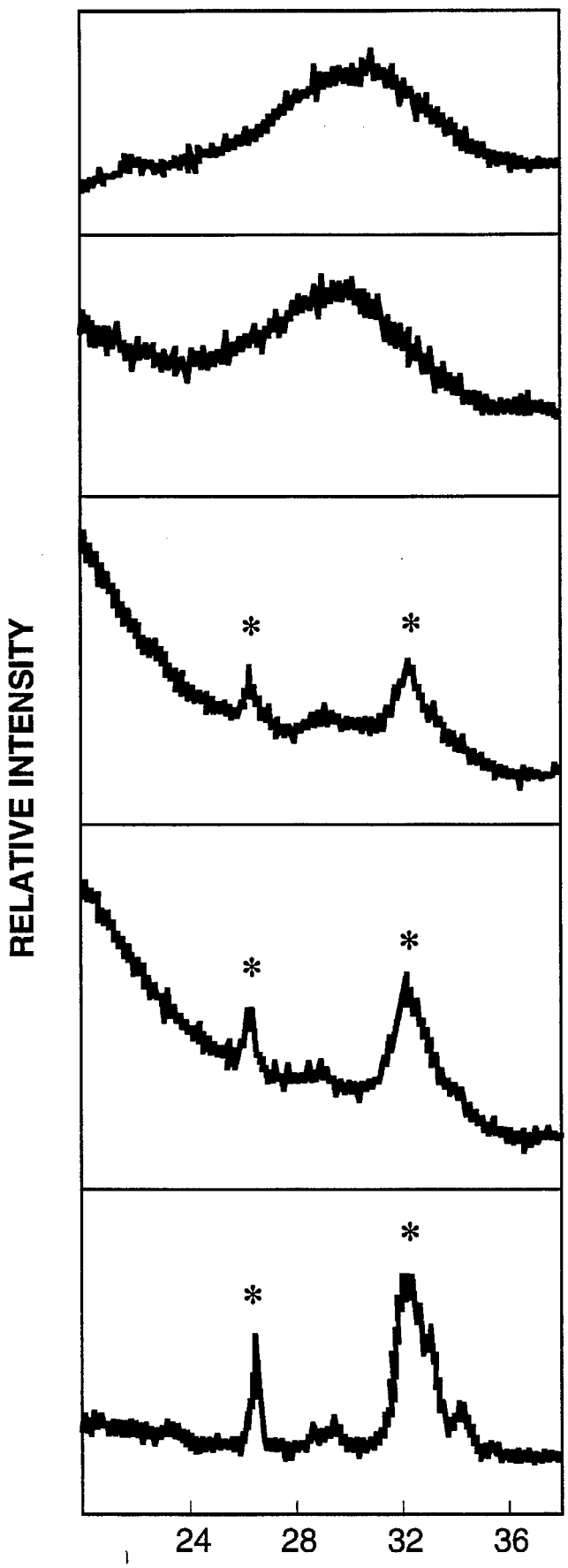

FIG. 7A demostrates XRD patterns of $P_2O_7$-stabilized ACP solid.

FIG. 7B demonstrates XRD patterns of a disk prepared from 40 wt % of $P_2O_7$-ACP and 60 wt% resin IV before soaking.

FIG. 7C demonstrates XRD patterns of a disk prepared from 40 wt% of $P_2O_7$-ACP and 60 wt% resin IV after soaking for 200 hours.

FIG. 7D demonstrates XRD patterns of a disk prepared from 40 wt% of $P_2O_7$-ACP and 60 wt% resin IV after soaking for 700 hours.

FIG. 7E demonstrates XRD patterns of a disk containing unstabilized ACP after soaking for 290 hours.

DESCRIPTION OF THE PREFERRED EMBODIMENTS

Mineralizing Composition

The mineralizing compositions of the present invention may be used with skeletal tissue as long-term sealants, restorative compositions, remineralizing compositions, adhesives or cements. These mineralizing compositions include a mineralizing agent, a monomer system and optionally, but preferably, one or more stabilizers. Additional additives of the type frequently found in compositions used for the aforementioned purposes may also be incorporated into the compositions. Neither the compositions themselves nor the composites formed from the compositions, which are used to seal or repair broken, cracked, carious, or otherwise damaged skeletal tissue or to secure a prosthetic device are toxic to or adversely affect either the organism as a whole or the tissue surrounding the site at which the composite is located.

Depending upon the intended application of the composite, the rate of release of ions from the polymeric matrix to form the HAP at the surface of and/or within the bone or tooth and the strength of the HAP, as well as the strength of the composite itself, may be varied. As discussed below, the factors which affect these characteristics include the concentrations of the monomer system and mineralizing agent; the presence of a stabilizer and, when used, its concentration; the nature of the polymeric matrix and, therefore, the nature of the monomer system; and the particle size of the powdered mineralizing agent in the mineralizing composition.

The concentration of the mineralizing agent is, by weight, about 1 to about 85%, preferably about 10 to about 80%, and most preferably about 40 to about 50%, based upon the total weight of the mineralizing composition. The concentration of the monomer system, which includes all compounds which undergo polymerization in the polymerizing reaction, including those having one or more unsaturated moieties which take part in the polymerization reaction and those which function as cross-linking agents as well as those undergoing simple polymerization, is, by weight, based on the total weight of the mineralizing composition, about 99 to about 15%, preferably about 90 to about 20%, and most preferably about 60 to about 50%.

Where the composite of the present invention is to be used for restorative purposes, it is generally desirable to use a higher proportion of mineralizing agent and a lower proportion of monomer system. Thus, the composite which results is capable of releasing more mineralizing agent over a longer period of time for the intended restoration. Conversely, when used as a sealant, i.e., as a conformational coating to prevent attack of a tooth from a cavity-forming substance and to fill fissures and cracks, a lower concentration of the mineralizing agent filler is preferred. Generally, a concentration of the mineralizing agent of about 1 to about 50% is preferred when the composition is employed as a sealant.

Mineralizing Agent:

Amorphous calcium phosphate is preferred as the mineralizing agent for the formation of HAP in the present invention. Because of both thermodynamic and kinetic effects, ACP readily dissolves in aqueous systems to form stable, crystalline structures of HAP, one of the major components of bones and teeth.

As discussed above, one of the factors which determines the rate of release of the mineralizing agent from the polymeric structure of the composite is the particle size and surface area of the mineralizing agent employed. The particle size of the mineralizing agent and the hydrophilicity or the permeability of the polymeric matrix, discussed below, are generally interrelated. Thus, where the polymeric matrix is highly hydrophilic or highly permeable to aqueous solutions of inorganic ions, a larger particle size of the mineralizing agent is preferred to avoid too rapid a release of ions. The sustained long-term release or interdiffusion of mineralizing agent from the polymeric matrix to the tooth surface takes place within a period of about 2 weeks to at least about 6 months, preferably about 2 weeks to at least about 1 year and most preferably about 2 weeks to at least about 2 years. The desired upper limit for the duration of interdiffusion and mineralization may vary with the particular application intended. Thus, once the characteristics of the polymeric matrix are selected and the monomer system and concentrations chosen to achieve the intended hydrophilicity or permeability, the particle size of the mineralizing agent may be selected accordingly. Generally, a particle size of the mineralizing agent, particularly when ACP is employed, is about 0.02 to about 50 μm, preferably about 0.03 to about 30 μm. When employed as a sealant, the particle size is preferably about 0.1 μm to about 50 μm.

Stabilizers:

Although ACP itself provides satisfactory solubility and mineralization rates, the inclusion of a stabilizer or stabilizing agent with the inorganic mineralizing agent provides several benefits. The stabilizer extends the lifetime of ACP by seeming to "poison" or inhibit the self-crystallization of the ACP and mineralization within or on the polymeric matrix. This appears to result from the adsorption to and blocking of sites in or on the ACP and the polymeric matrix where nucleation or precipitation of HAP occurs. As a result, higher concentrations of calcium and phosphate ions exist in solution, to the point of forming supersaturated solutions, such that precipitation at a tooth or bone surface occurs at a suitable and fairly constant rate. In effect, the stabilizers may be regarded as biomineralization regulatory agents in that they influence the nature and rate of HAP formation by slowing the hydrolytic transformation of ACP into crystalline HAP.

Suitable stabilizers include both organic and inorganic materials. Typically and preferably, such stabilizing agents are non-toxic, do not adversely affect the release, diffusion, and migration of mineralizing ions or their redeposition in bone and tooth tissue, the monomer system, or polymeric matrix or anything in the biological environment in which they are placed. As was noted earlier, prior art compositions which react with or tie up one or more of the ions actively involved in mineralization, such as calcium and phosphate ions, tend to produce poor results. Accordingly, stabilizers selected should either demonstrate no tendency to remove calcium or phosphate ions from solution or should be used at concentrations which show little tendency to make calcium and phosphate ions unavailable for mineralization but should maximize ACP solution stability. The stabilizer should also be fairly soluble in aqueous solutions and form highly charged species therein. While these substances may be either organic or inorganic materials, the latter are preferred. Typical examples include compounds of magnesium, carbonate, pyrophosphate, citrate, organic bis-phosphonates, adenine, nucleotides, phospholipids and phosphoproteins. Preferred are magnesium, carbonate and pyrophosphate stabilizers. It is preferred to use soluble salts whose aqueous solutions have pH values close to neutrality as the stabilizers. Thus, for anionic stabilizers, alkali metal salts are preferred, such as sodium and potassium salts. Most preferred are the sodium or sodium hydrogen salts, as for example, $Na_4P_2O_7$ and $NaHCO_3$ are sources of $CO_3^{-2}$ and $P_2O_7^{-4}$ ions which are preferred anionic stabilizers. For inorganic cationic stabilizers, nitrates are preferred. For example, $Mg(NO_3)_2$ is a preferred stabilizer. The various stabilizing agents may be used individually or in combination, to the extent that they do not react with one another to produce adverse results.

Suitably, the stabilizer should be present in an amount sufficient to effect stabilization of the type discussed above but should not be of such a high concentration as to significantly reduce the concentration of calcium and phosphate ions in solution. By way of example, the molar ratio Ca/Mg in ACP is suitably from about 1:1 to about 5:1. Preferably, the ratio is about 1.5:1 to about 3:1 and most preferably the ratio is about 2:1. For pyrophosphate ions, $P_2O_7^{-4}$, concentrations of about 0.5 to about 3 mol % of the total anionic content of the ACP are suitable. Preferably concentrations of about 1 to about 3 mol % are employed with concentrations of about 2 mol % being most preferred. Concentrations much above 3 mol % cause some $P_2O_7^{4-}$ to migrate to a bone or tooth surface and adversely affect mineralization at that surface.

Carbonate ion, $CO_3^{-2}$, may be incorporated in the ACP at concentrations up to but not including the concentration which would precipitate $CaCO_3$. Suitably, when in solutions used to prepare ACP the concentration of $CO_3^{-2}$ should be at least about 15 mmol/L, preferably at least about 100 mmol/L and most preferably about 180 mmol/L.

Methods of Preparing Mineralizing compositions:

The literature has reported a number of methods of preparing amorphous calcium phosphate. A preferred method involves the combination, in aqueous solution, with stirring, of a water soluble calcium compound, such as calcium nitrate, with a water soluble phosphate, such as trisodium phosphate or, more preferably, disodium hydrogen phosphate. Thus, a solution of $Ca(NO_3)_2$ is combined with a $Na_2HPO_4$ solution. After filtration or centrifugation, the solid precipitate is washed with ammoniated water, and lyophilized.

Stabilized ACP preparations are prepared similarly. Generally, a solution of the stabilizing agent is combined with either the calcium salt-containing solution or the phosphate salt-containing solution prior to mixing. For example, the $P_2O_7^{-4}$ ion stabilized ACP solution may be prepared in the same manner as the unstabilized ACP solution with the difference that some $Na_2HPO_4$ is substituted with the corresponding amount of $Na_4P_2O_7$.

In preparing the Mg-stabilized ACP, precipitation is initiated under conditions which maximize the solution stability of ACP. Thus, a solution of $Ca(NO_3)_2$ and $Mg(NO_3)_2$ of suitable volumes and concentrations may be combined to achieve the appropriate molar ratio of Ca/Mg. The resulting solution may be combined with a NaOH-containing solution of $Na_2HPO_4$. The concentration of NaOH is such as to achieve a pH of at least 10 after precipitation. Separation and drying are performed in the same manner as in the preparation of unstabilized ACP. Preparation of $CO_3$-containing ACP may be accomplished by mixing solutions of $Ca(NO_3)_2$, $Na_2HPO_4$ and $NaHCO_3$. The solutions are generally mixed to approach equilibrium from the basic side in order to minimize the loss of carbonate. Typically this involves combining the $Na_2HPO_4$ and $NaHCO_3$ solutions and adjusting the pH to be greater than 10 by addition of NaOH which will produce a post precipitation pH greater than 8.5. The $Ca(NO_3)_2$ solution is then slowly added to the alkaline solution to obtain a precipitate. After centrifugation, the product is treated as in the other stabilized preparations of ACP.

Unsaturated Monomer System

In addition to the powder or particulate mineralizing agent, the compositions of the present invention also include an unsaturated monomer system. One or more monomers are employed which form, upon polymerization, a three-dimensional matrix that is suitable for incorporating the particulate mineralizing agent and any stabilizing agent within the matrix.

Monomers:

Several of the requirements of the unsaturated monomers employed are that they and the polymers which they form are relatively non-toxic and are capable of being quickly and easily cured at temperatures close to human body temperature. It is generally desirable that they not react chemically with the mineralizing agent so as to deplete the agent of ions taking part in the mineralizing process. It is also desirable that the monomers not react with the HAP formed, any biological tissue present or any appliance or prosthesis present except where there is a specific intention to do so. The monomers are also selected to provide suitable strength to the cured polymeric matrix as well as to provide sufficient diffusion or permeability of water and dissolved mineralizing agent, stabilizing agent and other water soluble additives through the polymeric matrix formed by the monomer system. It is also preferred that the monomer system be so chosen as to provide controlled hydrophilic properties to the polymeric matrix.

Broadly, monomers having acrylate or methacrylate moieties are most suitable for the invention. While acrylate compounds could be used in the present invention since their chemical and physical properties are similar to the methacrylate monomers and polymers, as a group, they are generally less suitable since some of the acrylate compounds demonstrate higher toxicity levels.

Preferred as the unsaturated monomers of the monomer system of the present invention are methacrylate monomers. Most preferred are salts and esters of methacrylate monomers. These include monofunctional and polyfunctional monomers, that is, they contain one or a plurality of unsaturated units or methacrylate groupings.

The monomers selected to form the polymeric matrix are chosen based on the properties sought in the matrix. Thus, the polymeric matrix must provide sufficient strength to withstand the forces normally encountered in dental and orthopedic situations where the affected site is subjected to a range of stresses. This may be achieved by employing monomers having a rigid and tough backbone structure. Such monomers include those which are both monofunctional or polyfunctional with regard to the number of methacrylate moieties present.

It is preferred that the monomer system include at least one compound having two or more functional groups capable of reacting with functional groups present on the polymeric chain. Thus, in its simplest form, the monomer system of the present invention may include a single monomer having a rigid backbone and a single unit of unsaturation which, upon polymerization, would form a homopolymer having sufficient strength and rigidity to act as a polymeric matrix. Another simple, yet more preferred, embodiment of the invention includes a monomer system using a single monomer having at least two units of unsaturation, preferably each a methacrylate moiety. In such an instance, a cross-linked three-dimensional structure would be formed upon polymerization. In such an instance, while forming a homopolymer, some of the monomer would function as a cross-linking agent.

In other preferred embodiments of the present invention, polymeric matrices could be formed from monomer systems employing mixtures of monomers in which one or more monomers would have two or more units of unsaturation to function as a cross-linking agent for other monomers having the same or fewer units of unsaturation.

While the more cross-linking which exists, the greater is the strength of the polymeric matrix and the more three-dimensional character it has, the improvement in strength is off-set by a decrease in permeability or diffusion of water and dissolved solutes. Conversely, a more "open" structure favors interdiffusion of aqueous solutions of the ions present between the polymeric matrix and the tooth or bone surface as well as the surrounding environment of the body. Accordingly, a monomer system is so selected as to provide the necessary strength in the polymeric matrix to suit the purpose intended for the composite, preferably by including at least one monomer with a rigid backbone and/or by incorporation of a cross-linking agent which is itself a monomer having a plurality of units of unsaturation, preferably being methacrylate moieties. To achieve the interdiffusion or interpermeation sought in the polymeric matrix, a monomer with hydrophilic properties may be included and/or the amount of cross-linking agent included in the monomer system is so selected as to not severely inhibit the sustained, and effectively timed release of mineralizing agent from the polymeric matrix.

Amongst the groups which impart hydrophilic properties to the polymeric matrix and which are preferably present in at least one of the monomers employed in the monomer system are hydroxyl groups, ethylene oxide groups, amine groups or carboxylic acid groups. The latter group in high concentrations may upset the balance of calcium and phosphate ions by tying up too many calcium ions. In their salt or carboxylate form, however, carboxylic acid monomers can be used as comonomers.

Although, as indicated above, the monomeric system of the present invention could contain a single monomer having a single unit of unsaturation where the backbone of the monomer is sufficiently rigid, it is preferred that when a single monomer is employed it have at least two units of unsaturation, such that at least some of the monomer employed functions as a cross-linking agent. In most instances, it is preferred that a plurality of monomers be employed, at least one of which is capable of functioning as a cross-linking agent in that it has two or more units of unsaturation.

As previously indicated, the preferred monomers of the present invention are methacrylate compounds, preferably esters and salts of methacrylic acid. Amongst the former are alkyl esters of methacrylic acid wherein the alkyl group contains 1 to about 100 carbon atoms, preferably about 1 to 10 carbon atoms. Of these, triethyleneglycol and decamethylene dimethacrylate are most preferred. Hydroxyalkyl methacrylates in which the alkyl group contains 2 to 10 carbon atoms are also preferred. Such hydroxy compounds provide hydrophilic characteristics to the polymeric matrix and are preferably used in combination with another monomer having at least two units of unsaturation. Examples of hydroxyalkyl methacrylates preferred for the present invention include 2-hydroxyethyl methacrylate (HEMA), the various isomers of hydroxypropyl methacrylate (HPA), and glyceryl monomethacrylate. The use of HEMA and similar monomers in the monomer system produces a polymeric matrix which promotes bonding to organic or inorganic components of enamel and dentin. Suitable methacrylate compounds having a plurality of methacrylate groups include those which are derivatives of polyols. Among the simpler compounds are glyceryl dimethacrylate and glyceryl trimethacrylate. The latter compound, having three methacrylate groups, functions as a coupling or cross-linking agent to promote strength while the former compound, having two methacrylate moieties and a single hydroxyl group provides both hydrophilic properties as well as functioning as a cross-linking agent. Glyceryl monomethacrylate imparts even greater hydrophilic properties to the polymeric matrix. Combinations of 2 or more of these 3 compounds could be used with some advantage in providing the necessary strength and hydrophilic properties to the polymeric matrix of the present invention. They may also be used in combination with other methacrylate compounds of the present invention. Diethyleneglycol dimethacrylate (DEGDMA) and triethyleneglycol dimethacrylate (TEGDMA) are preferred low molecular weight monomers which reduce viscosity in the mineralizing compositions of the present invention. Another type of polyol compound which is preferred in the present invention is one which is derived from phenolic compounds. An example of such a compound which is preferred in the present invention is 2, 2-bis [para-(2'-hydroxy-3'-methacryloxypropoxy) phenyl]-propane (Bis-GMA). This is a high molecular weight monomer which is a viscous liquid having a fairly rigid backbone.

Another class of methacrylate compounds mentioned above includes salts of methacrylic acid. These include the water-soluble methacrylate salts of the alkali and alkaline earth metals, such as sodium, potassium, and calcium, which demonstrate hydrophilic properties. Zirconyl dimethacrylate (ZrM) is a preferred cross-linking agent and, in addition to functioning as a suitable coupling agent, also mediates inorganic particle-resin adhesion.

Examples of other unsaturated monomers which can be used in the present invention include the following methacrylic and non-methacrylic compounds: acenaphthylene, 1,6-hexamethylene dimethacrylate, 1, 10-decamethylene dimethacrylate, benzyl methacrylate, butanediol monoacrylate, 1,3-butanediol diacrylate (1,3-butylene glycol diacrylate), 1,3 butylene glycol dimethacrylate), 1,4-butanediol diacrylate, 1,4-butanediol dimethacrylate, n-butyl acrylate, n-butyl methacrylate, t-butyl acrylate, t-butyl methacrylate, n-butyl vinyl ether, t-butylaminoethyl methacrylate, 1,3-butylene glycol diacrylate, cyclohexyl acrylate, cyclohexyl methacrylate, n-decyl acrylate, n-decyl methacrylate, diethylene glycol diacrylate, diethylene glycol dimethacrylate, dipentaerthritol monohydroxypentaacrylate, 2-ethoxyethoxyethyl acrylate, 2-ethoxyethyl methacrylate, ethoxylated bisphenol A diacrylate, ethoxylated bisphenol A dimethacrylate, ethoxylated trimethylolpropane triacrylate, ethyl methacrylate, ethylene glycol dimethacrylate, 2-ethylhexyl acrylate, 2-ethylhexyl methacrylate, furfuryl methacrylate, glyceryl propoxy triacrylate, 1,6 hexanediol diacrylate, 1,6 hexanediol dimethacrylate, n-hexyl acrylate, n-hexyl methacrylate, 4-hydroxybutyl acrylate, (butanediol monoacrylate), 2-hydroxyethyl acrylate, hydroxyethyl methacrylate, hydroxypropyl acrylate, hydroxypropyl methacrylate, isobornyl acrylate, isobornyl methacrylate, isobutyl acrylate, isobutyl methacrylate, isobutyl vinyl ether, isobutyl acrylate, isobutyl methacrylate, isobutyl vinyl ether, isodecyl acrylate, isodecyl methacrylate, isooctyl acrylate, isopropyl methacrylate, lauryl acrylate, lauryl methacrylate, maleic anhydride, methacrylic anhydride, 2-methoxyethyl acrylate, methyl methacrylate, neopentyl acrylate, neopentyl methacrylate, neopentyl glycol diacrylate, neopentyl glycol dimethacrylate, n-octadecyl acrylate, (stearyl acrylate), n-octadecyl methacrylate, (stearyl methacrylate), n-octyl acrylate, pentaerythritol tetraacrylate, pentaerythritol triacrylate, 2-phenoxyethyl acrylate, 2-phenoxyethyl methacrylate, 2-phenylethyl methacrylate, phenyl methacrylate, polybutadiene diacrylate oligomer, polyethylene glycol 200 diacrylate, polyethylene glycol 400 diacrylate, polyethylene glycol 200 dimethacrylate, polyethylene glycol 400 dimethacrylate, polyethylene glycol 600 dimethacrylate, polypropylene glycol monomethacrylate, propoxylated neopentyl glycol diacrylate, stearyl acrylate, stearyl methacrylate, 2-sulfoethyl methacrylate, tetraethylene glycol diacrylate, tetraethylene glycol dimethacrylate, tetrahydrofurfuryl acrylate, tetrahydrofurfuryl methacrylate, n-tridecyl methacrylate, triethylene glycol diacrylate, triethylene glycol dimethacrylate, trimethylammoniumethacrylic chloride, trimethylolpropane triacrylate, trimethylolpropane trimethacrylate, 3-methacryloxypropyltrimethoxysilane, trimethylsilylmethacrylate, (trimethylsilylmethyl)methacrylate, tripropylene glycol diacrylate, tris(2-hydroxyethyl)isocyanurate triacrylate, vinyl acetate, vinyl caprolactam, n-vinyl-2-pyrrolidone, zinc diacrylate, zinc dimethacrylate.

Another embodiment of the present invention substitutes a prepolymer or oligomer for some of the monomer used. The oligomers used are miscible with the monomers mentioned above. Preferably the oligomers are formed from one or more of the same monomers employed in the monomer system.

Free Radical Initiator:

Since most of the polymerization reactions which unsaturated compounds undergo, particularly methacrylate compounds, proceed by a free radical mechanism, a free radical initiator is generally included in the monomer system. Any free radical initiator which is substantially non-toxic in the amounts employed in the composition; which does not react adversely with either the polymeric matrix, once formed, components of the mineralizing agent or stabilizing agent or with any appliance or prosthesis; and which is of sufficient activity at body temperature, under the conditions used, to effect curing of the monomer system to form a sufficiently rigid polymeric matrix within a period of 30 seconds to several hours, preferably in less than one to eight minutes, is suitable for use in the present invention. The free radical initiator may be of the chemical type (redox system) in which a peroxide initiator and a polymerization accelerator react at ambient temperatures to initiate the polymerization of the monomer system. Alternatively, a photoinitiator system may be used in which light, such as ultraviolet light, but preferably the visible portion of the spectrum, is employed as the energy source to stimulate the free radical initiator. The former type is sometimes preferred for use with prosthetic devices. Examples of such chemical initiators include hydroperoxides, peresters or peroxides such as benzoyl peroxide, or amines, preferably tertiary aromatic amines, such as N,N-dimethyl toluidine may be used. Preferably a one part system using a visible light photoinitiator is employed. Suitable photoinitiators include benzil 2,3-butanedione, phenyl-1,2-propandione, and camphorquinone (CQ).

The monomer system may also include a polymerization accelerator, such as ethyl-4-N,N-dimethylamino benzoate or N,N-dimethylaminoethyl methacrylate.

In addition to the components discussed above, it is frequently desirable to include with the mineralizing agent various types of fillers and additives. Thus, silica, glass or silanized glass particles may be included, preferably replacing some of the mineralizing agent, to provide additional strength. Typically, such a composition might employ, by weight, about 20% silanized glass and about 20% ACP. Inorganic fluorine compounds may be included for the beneficial effects provided by fluoride ions. Such compounds are of the type typically found in fluorinated toothpaste, such as sodium fluoride, potassium fluoride, erbium fluoride, yttrium fluoride, titanium fluoride, zirconium fluoride, sodium fluorophosphate, and calcium fluorophosphate. In addition, other therapeutic agents such as antibiotics or other medicaments may be included to treat a specific condition.

Monomer System:

The mineralizing compositions of the present invention are generally compounded in the same manner as are conventional dental compositions used as sealants, cements or restorative compositions which contain a monomer or resin and a filler. That is, the mineralizing agent of the present invention, along with any stabilizer and other additives, is combined with the monomer system, which is typically a liquid. The components are blended to form a paste of uniform dispersion and consistency. Surface-active agents such as organo-silanes, -titanates, -aluminates, -zirconates, etc. applied to the mineralizing agent prior to or during mixing with the monomer system are especially suitable for achieving optimal dispersion and consistency. The paste is applied to the bone or tooth as a similar conventional composition used for the same purpose. If pressure and/or exposure to light are required prior to or during the curing process, conventional methods and/or sources may be employed.

Mineralizing Composite:

The composites of the present invention are formed so as to provide sustained release of mineralizing ions for a period of from about 10 days to at least about 6 months. Preferably sustained release is maintained for at least about 1 year and most preferably, the composites of the present invention release mineralizing agent for a period of at least about 2 years. Thus, while for certain applications it may be acceptable or even preferred to have release of mineralizing agent occur for periods of several weeks, in many instances longer duration is desirable. By "sustained release" of mineralizing agent is meant approximately steady state or constant concentration of ions from the mineralizing agent diffusing through, and migrating from, the polymeric matrix. While concentrations may vary slightly from day to day, over a period of time, the concentration remains approximately constant. The type of sustained release being referred to herein is illustrated in FIGS. 3 through 5B.

The mineralizing composites of the present invention include the same inorganic particulate mineralizing agent incorporated within a polymeric matrix as are combined with the monomer system of the mineralizing composition. The polymeric matrix is preferably cross-linked. The polymeric matrix is also of sufficient hydrophilicity and/or permeability to permit interdiffusion of aqueous solutions, such as solutions of $Ca^{+2}$ and $PO_4$ ions, between the polymeric matrix and a tooth or bone surface.

As indicated above, the characteristics of the composite may be altered by appropriate selection of the monomer system and mineralizing agent, as well as such variables as the concentration of such components and particle size of the mineralizing agent, and stabilizer, when employed, as well as the additives included in the composite. Thus, all other things being equal, when the proportion of monomer system increases relative to the amount of mineralizing agent, the strength of the composite increases. However, when larger amounts of mineralizing agent are required, such as in restoration where relatively large amounts of apatite formation are required over a protracted period of time, some strength is sacrificed to provide for incorporation of a larger proportion of mineralizing agent. In such instances, a filler which provides additional strength, such as silica, glass, or silanized glass may be incorporated into the matrix along with the mineralizing agent and, where used, stabilizing agent.

The examples set forth below are intended to be exemplary only and should not be construed as in any way limiting the scope of the present invention.

EXAMPLE 1

Preparation of ACP:

Unstabilized ACP was prepared by rapidly adding 125 ml of a solution containing 800 mmol/L of $Ca(NO_3)_2$ to an equal volume of a solution containing 536 mmol/L of $Na_2HPO_4$. The latter solution was brought to a pH of 12.5 with 1 mol/L of NaOH prior to mixing with the $Ca(NO_3)_2$. The reaction was conducted at 22° C. in a closed system (under nitrogen) in order to minimize $CO_2$ adsorption. After filtration, the solid phase was washed with ammoniated water having a pH of 10.5, and lyophilized.

EXAMPLE 2

Preparation of ACP Stabilized with $P_2O_7^{-4}$:

ACP stabilized with $P_2O_7^{-4}$ ions was prepared in the same manner as was ACP in Example 1, except that 2 mol% of $Na_4P_2O_7$ was substituted for the corresponding amount of $Na_2HPO_4$.

EXAMPLE 3

Preparation of ACP Stabilized with $Mg^{+2}$:

In the preparation of Mg-containing ACP, precipitation was initiated under conditions which maximized the solution stability of the ACP. A solution was prepared by mixing 110 ml of solution containing 750 mmol/L of $Ca(NO_3)_2$ and 55 ml of solution containing 750 mmol/L of $Mg(NO_3)_2$ (molar ratio Ca/Mg=2:1). The combined solution was mixed with 250 ml of a NaOH solution containing 250 mmol/L $Na_2HPO_4$ solution (molar ratio NaOH:$Na_2HPO_4$=1.1:1). The slight excess of NaOH was necessary to achieve a pH of at least 10 in the supernatant liquid after precipitation. Separation of the solid phase and subsequent drying was performed essentially as described in Example 1.

EXAMPLE 4

Peparation of ACP Stabilized with $CO_3-2$:

A solution was prepared containing 14.1 mmol/L $Na_2HPO_4$ and 180 mmol/L of $NaHCO_3$. The initial pH of the $Na_2HPO_4$/$NaHCO_3$ solution was adjusted to at least 10 by addition of NaOH in order to obtain a pH after precipitation of the supernatant liquid of at least 8.5. To 500 ml of the $Na_2HPO_4$/$NaHCO_3$ solution, at room temperature, was slowly added with stirring, 500 ml of a solution containing 20 mmol/L of $Ca(NO_3)_2$ solution. The calcium nitrate solution was added to the sodium hydrogen phosphate/bicarbonate solution so that the equilibrium was approached from the basic side in order to minimize the loss of carbonate. After full development of the precipitate (within about 5 minutes), the suspension was centrifuged, washed with ice-cold ammoniated water, at a pH of about 10.5, and lyophilized.

EXAMPLE 5

General Method of Preparing Speciman Disks:

Paste compositions were prepared according to the method of the present invention containing, by weight based on the total weight of the composition, 40% inorganic solids (mineralizing composition or HAP) and 60% resin (monomer system), by hand spatulation. (The specific materials employed are described below in Examples 6 to 10.) After the inorganic phase was uniformly dispersed in the organic phase to form a "homogenized" paste, the paste was maintained under moderate vacuum in a vacuum desiccator at a pressure of 2 to 4 KPa overnight to eliminate any air entrained during the mixing. The elimination of entrained air also eliminates undesirable development of porosity in the polymeric matrix. Any entrained oxygen also inhibits free radical polymerization. The paste was then pressed into a circular teflon mold, supported at the bottom end with a thin mylar film backed by a 1 mm glass plate. After covering the top of the mold with a similar film and glass support, the mold assembly was clamped and irradiated on each side for 120 seconds with visible light, using a light source known as Prismatics Lite (available from L.D. Caulk Dentsply, Milford, Del., U.S.A.), to form a composite disk having a diameter of 15.8 to 16.8 mm and a thickness of 1.5 to 2.1 mm in thickness. After postcuring at 37° C. in air for 15 to 18 hours, the disks were weighed and examined by X-ray defraction (XRD) or subjected to various tests such as soaking tests to determine the amount and/or the rate of release of mineralizing agent and/or stabilizing agent. Other tests included measurement of mechanical strength by a biaxial flexure test according to Wachtman et al. (J. Mat., 7, 188 (1972)).

TABLE 1

Composition of the resins used for the preparation of composite disk specimens.

| Resin formulation | Resin composition (wt %) | | | | | |
|---|---|---|---|---|---|---|
| | Bis-GMA | TEGDMA | HEMA | ZrM | CQ | 4E |
| I | 49.5 | 49.5 | — | — | 0.2 | 0.8 |
| II | 35.5 | 35.5 | 28.0 | — | 0.2 | 0.8 |
| III | 49.1 | 49.1 | — | 0.8 | 0.2 | 0.8 |
| IV | 35.1 | 35.1 | 28.0 | 0.8 | 0.2 | 0.8 |

Bis-GMA = 2,2-bis[para-(2'-hydroxy-3'-methacryloxypropoxy)phenyl]-propane
TEGDMA = triethyleneglycol dimethacrylate
HEMA = 2-hydroxyethyl methacrylate
ZrM = zirconyl dimethacrylate
CQ = camphorquinone

TABLE 2

Types of calcium phosphates used as fillers in the preparation of composite disk specimens.

| | Calcium Phosphate | Concentration of Stabilizer | $Ca^{+2}/PO_4$ |
|---|---|---|---|
| A | HAP | 0 | 1.54 ± 0.04 |
| B | Unstabilized ACP | 0 | 1.41 ± 0.06 |
| C | ACP/magnesium | 33 mol % | 1.45 ± 0.05* |
| D | ACP/carbonate | 25 wt % | 2.58 ± 0.10 |
| E | ACP/pyrophosphate | 2 mol % | 1.38 ± 0.06 |

*Given value corresponds to $(Ca^{2+} + Mg^{2+})/PO_4$ ratio.
HAP = haphydroxyapatite

EXAMPLE 6

Immersion Test of Specimen Disks:

Specimen disks were prepared as described in Example 5 employing the monomer systems (I–IV) described in Table 1 and the different inorganic filler compositions (A–E) described in Table 2. The specimen disks were immersed in continuously stirred N-(2-hydroxyethyl)piperazine-N1-2-ethanesulfonic acid (HEPES) buffered (pH=7.4) NaCl solutions having an ionic strength of 0.129 mol $Dm^{-3}$ (240 mOsm) at 37° C. The release of $Ca^{+2}$ and $PO_4$ ions from the disk were followed kinetically for up to 500 hours. Concentrations of $Ca^{+2}$ ion (and $Mg^{+2}$ ion in systems using Mg-stabilized ACP) were measured by atomic adsorption spectrophotometry. Concentrations of $PO_4$ in solution were determined by U.V. spectrophotometry.

After completion of the immersion tests, the disks were removed and characterized by XRD, as they were prior to immersion. The disks were also weighed and tested for mechanical strength. The immersion solutions remaining after removal of the disks were seeded with 0.7 m/ml HAP crystals and aliquots taken at regular intervals were filtered (using a 0.22 μm filter) and the filtrate analyzed for $Ca^{+2}$ and $PO_4$ as were the solutions prior to seeding.

Figure 1:
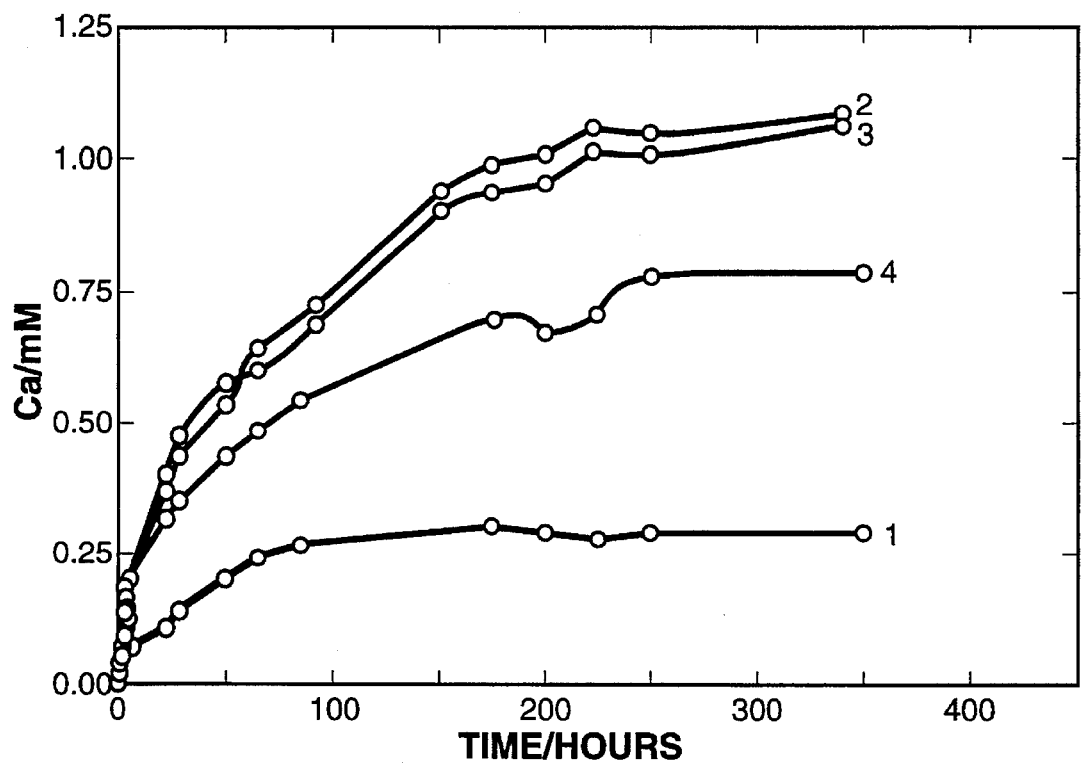
FIG. 1 graphically shows $Ca^{2+}$ release in pH 7.4 buffered solutions during soaking of disks composed of $P_2O_7$-stabilized ACP and different polymerized resins: Bis-GMA+TEGDMA (1), Bis-GMA+TEGDMA+HEMA (2), Bis-GMA+TEGDMA+ZrM (3) or Bis-GMA+TEGDMA+HEMA+ZrM (4).
Figure 2:
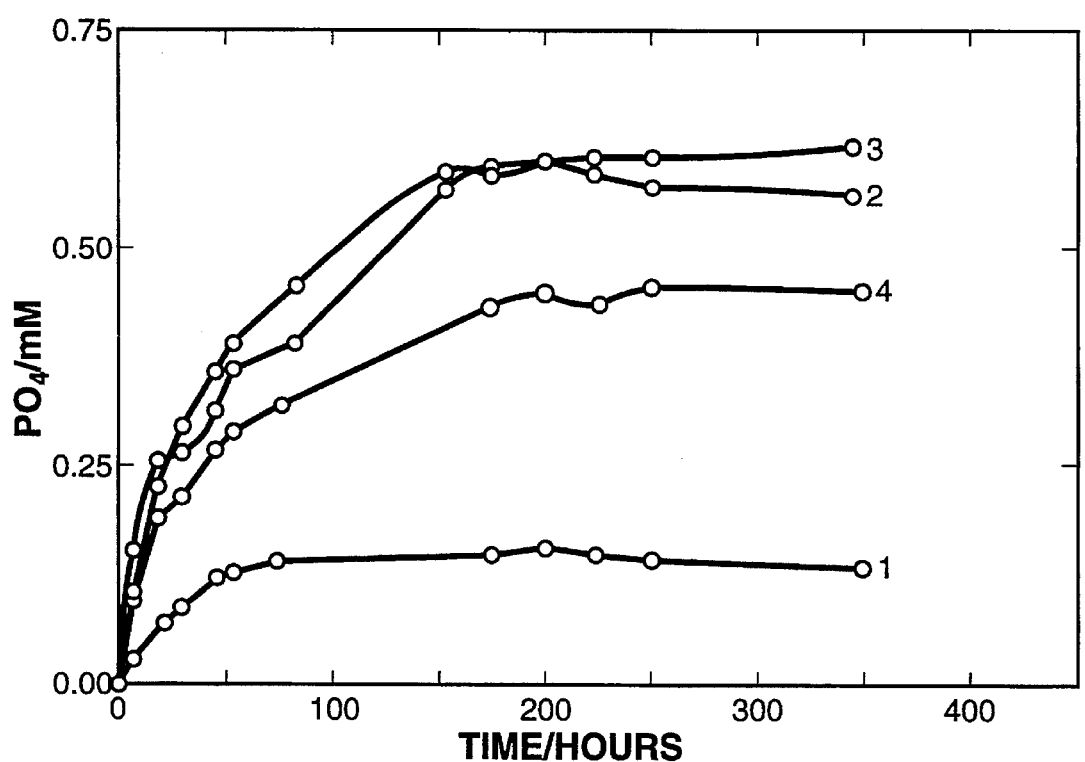
FIG. 2 graphically illustrates the effect of the resin compositions indicated in FIG. 1, on total $PO_4$ ion concentrations from composite disks containing $P_2O_7$-stabilized ACP.

As shown in FIGS. 1 and 2, the concentration levels of released $Ca^{+2}$ and $PO_4$ ions from test disks containing ACP stabilized with $P_2O_7^{-4}$ were significantly affected by the resin composition. The solution concentrations of both the $Ca^{+2}$ and $PO_4$ ions significantly increased by adding HEMA, ZrM, or both to the basic resin components, Bis-GMA and TEGDMA. Based on these results, composites derived from all four components, Bis-GMA, TEGDMA, HEMA and ZrM (resin IV, Table 1) were used to obtain the additional findings described below.

Figure 3:
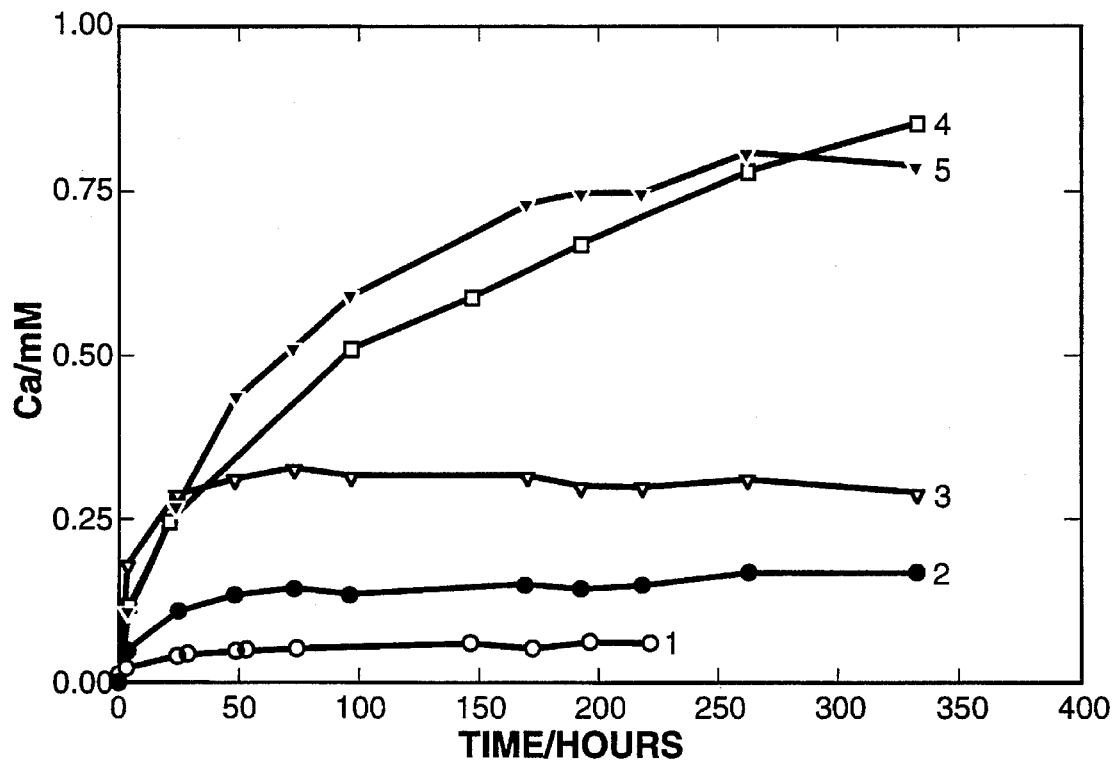
FIG. 3 graphically shows $Ca^{2+}$ release from (Bis-GMA+TEGDMA+HEMA+ZrM; resin IV) composites containing different calcium phosphates: HAP (A), unstabilized ACP (B), Mg-stabilized ACP (C), $CO_3$-stabilized ACP (D) or $P_2O_7$-stabilized ACP (E).
Figure 4:
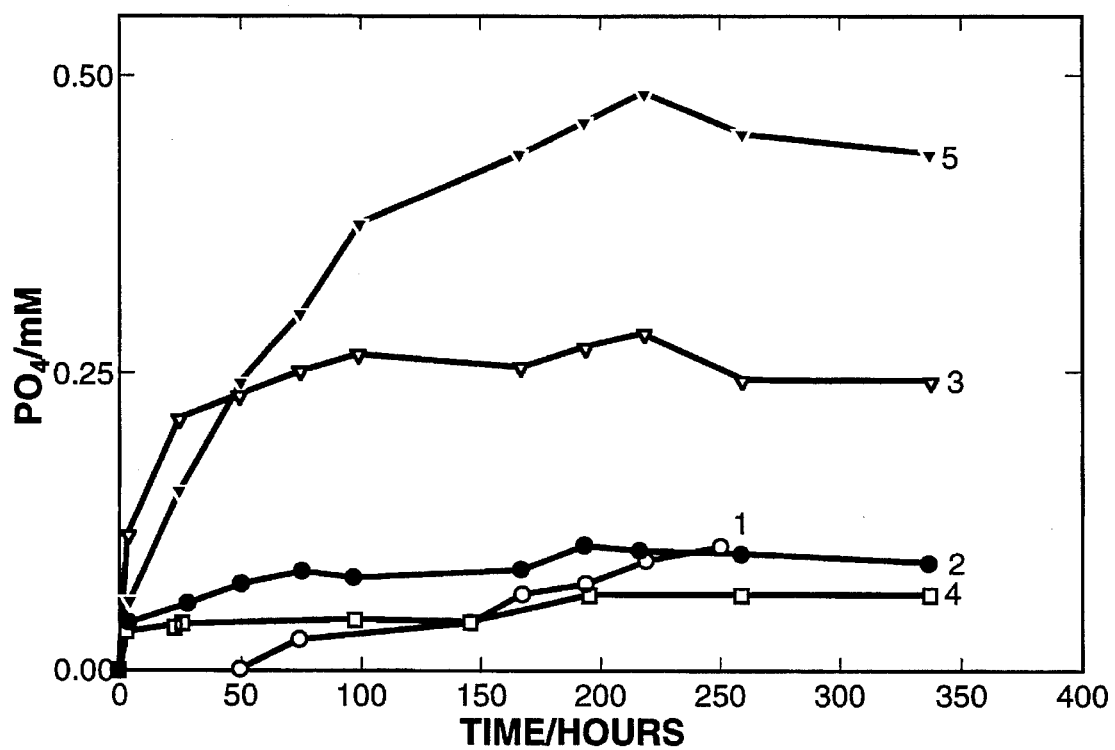
FIG. 4 graphically provides a comparison of total $PO_4$ ion release from disks made from resin IV and different calcium phosphates (as illustrated in FIG. 3).
Figure 5A:
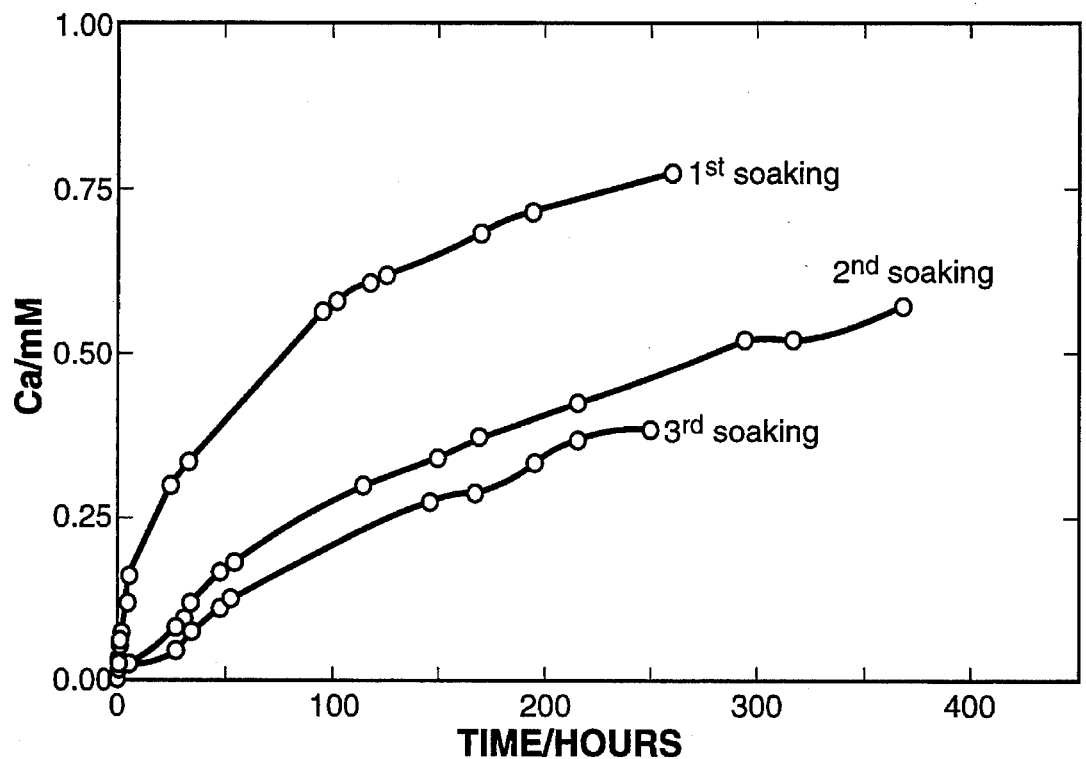
FIG. 5A describes graphically levels of $Ca^{2+}$ released during the initial immersion of a $P_2O_7$-stabilized ACP/composite IV disk and during two reimmersions of the same specimen ($2^{nd}$ and $3^{rd}$ immersion).
Figure 5B:
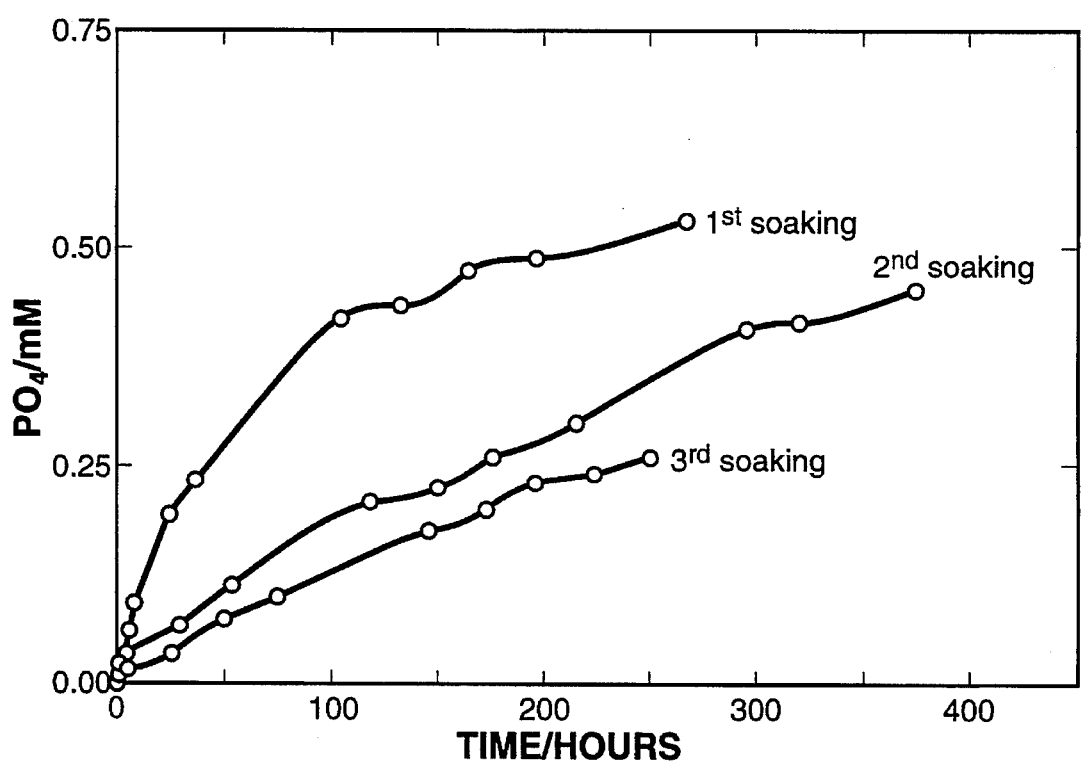
FIG. 5B describes graphically levels of total $PO_4$ released during the initial immersion of a $P_2O_7$-stabilized ACP/ composite IV disk and during two reimmersions of the same specimen ($2^{nd}$ and $3^{rd}$ immersion).
Figure 6B:
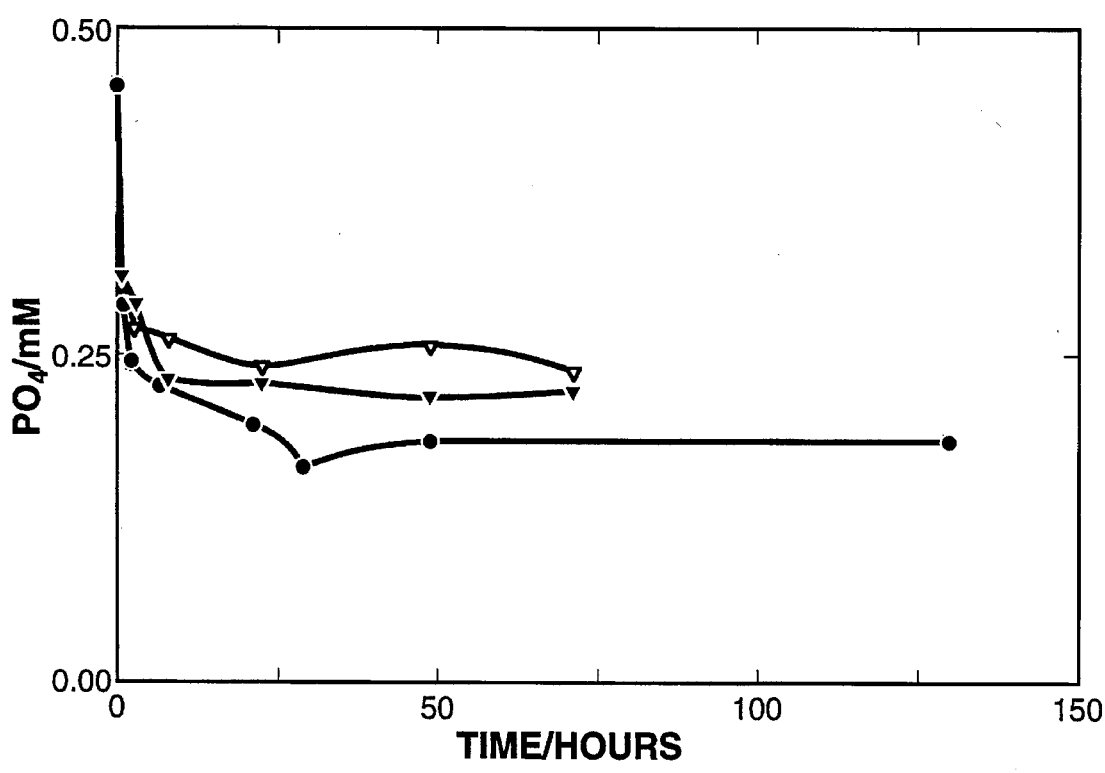

The time release profiles of $Ca^{+2}$ and $PO_4$ ions as a result of soaking disks composed of unstabilized ACP and $Mg^{+2}$, $CO_3^{-2}$ or $P_2O_7^{-4}$-stabilized ACP and resin IV in buffered aqueous solutions are illustrated in FIGS. 3 and 4. ACP stabilized with $Mg^{+2}$, $CO_3^{-2}$ or $P_2O_7^{-4}$ ions which slow the hydrolytic transformation of ACP into crystalline HAP, released $Ca^{+2}$ into solution at significantly higher levels compared to unstabilized ACP or compared to HAP. Levels of released $PO_4$ were similarly higher for $Mg^{+2}$ and $P_2O_7^{-4}$-stabilized ACP but lower for $CO_3^{-2}$-containing ACP Disks stabilized with $P_2O_7^{-4}$ were removed after immersion for 270 hours, rinsed, and placed in fresh buffer. They continued to release additional $Ca^{+2}$ and $PO_4$ at levels substantially higher than those observed for unstabilized ACP (FIGS. 5A and 5B). A third immersion and fresh buffer released calcium and phosphate ions at nearly the same level as the second immersion. Although stabilized ACP/resin formulations resulted in solution supersaturations that were considerably above the minimum necessary for remineralization (Table 3), the solution curves did not show any significant drop in $Ca^{+2}$ and $PO_4$ concentrations with time that would suggest that disk-induced remineralization occurred. However, reprecipitation started immediately upon introduction of exogenous HAP crystal seeds (FIGS. 6A and 6B).

TABLE 3

Thermodynamic Stability of $Ca^{+2}$ and $PO_4$ Solution

| | Calcium Phosphate | Ion activity product, IAP $IAP = (Ca^{+2})^{10}(PO_4)^6(OH^-)^2$ | ΔG (kJ/mol) $\Delta G = -(RT/n)\ln(IAP/K_{sp})$[1] |
|---|---|---|---|
| A | HAP | $9.12 \ 10^{-117}$ | $-0.353$[2] |
| B | Unstabilized ACP | $1.36 \ 10^{-112}$ | $-1.728$ |
| C | ACP/magnesium | $8.71 \ 10^{-108}$ | $-3.314$ |
| D | ACP/carbonate | $8.51 \ 10^{-107}$ | $-3.640$ |
| E | ACP/pyrophosphate | $2.24 \ 10^{-102}$ | $-5.097$ |

[1]R is the ideal gas constant, T is the absolute temperature, n is the number of ions in the ion activity product and $K_{sp}$ is the thermodynamic solubility product of HAP (program provided value of 117.11 was used). Negative G values indicate supersaturation.
[2]The small, negative ΔG indicates that the HAP prepared for this study was slightly more soluble than stoichiometric HAP, a finding consistent with its lower $Ca/PO_4$ ratio (1.54 vs 1.67).

The thermodynamic stability is shown in Table 3 with respect to stoichiometric HAP of solutions in which the Ca and $PO_4$ ions released upon soaking various mineral filled-resin IV composite disks had reached their maximum concentrations. Gibbs free-energy, ΔG, was calculated by the solution equilibrium calculation program EQUIL (MicroMath Scientific Software, Salt Lake City, Utah, USA).

All of the specimen disks containing ACP were stable when kept dry. No signs of conversion to HAP were revealed by XRD. Upon immersion in aqueous buffer, conversion occurred more slowly when the ACP was stabilized. The XRD scans in FIG. 7A through 7E, clearly show the slow formation of HAP in a $P_2O_7^{-4}$-ACP-containing disk immersed in the buffer solution (scans FIGS. 7C and 7D in which HAP peaks are indicated by an asterisk) when compared to a similarly soaked disk containing unstabilized ACP (FIG. 7E). The amount of HAP remained low after 700 hours of soaking. The XRD showed that even this HAP was lost upon removing the outer third of the disk by grinding.

The above-described properties and results of tests performed on specimen disks show that stabilized ACP-containing methacrylate resins release high, sustainable levels of calcium and phosphate ions sufficient to reprecipitate as HAP crystals, of the type found in bone and tooth tissue. A unique, advantageous feature also revealed by the test results is that released ions do not reprecipitate on the composite itself. This property ensures that ions released from composite resins applied to tooth and bone surfaces are freely available for remineralization and are not lost through composite reincorporation. The test data further shows that the release of mineralizing ions occurs over extended time periods, substantially longer than can be realized with ACP-containing materials previously available. Such extended availability of mineralizing agent is particularly advantageous in long-term sealant, adhesive, and restorative uses where the prevention of tooth demineralization (e.g., in orthodontically treated teeth) or promotion of tooth remineralization (e.g., in white spots, carious lesions, root caries, etc.) can be achieved without frequent reapplication of the compounds, such as is currently the case with mineralizing toothpaste, rinses and gel coatings.

EXAMPLE 7

Test of mineralizing composites on tooth surfaces.

Caries-like enamel lesions were formed on extracted bovine incisors with a pH lactate (0.1 mol/L) solution containing 3 mmol/L $CaCl_2$, 1.8 mmol/L $KH_2PO_4$, and 1 wt % carboxymethylcellulose (Teranaka and Koulourides, Caries Res. 21:326–332(1987)). The demineralized teeth were sectioned and ground to a thickness of about 120 μm. Contact microradiographs of the sections were obtained with Ni-filtered Cukα radiation (Faxitron, Model 43855A, Hewlett Packard, McMinnville, Oreg.). Each section specimen was placed in a holder consisting of two tightly held glass plates with a layer of parafilm between each side of the section and the opposing glass surface. The exposed edge of the section containing the demineralized enamel surface was coated with a 1 mm thick layer of composite paste comprising of 40% ACP stabilized with $P_2O_7^{-4}$ and 60% type IV resin formulation and photocured for 120 seconds. The assembly containing the composite-coated tooth section was immersed in a remineralizing solution ([Ca]=1.2 mmol/L, [$PO_4$]=0.7 mmol/L, pH 7.0 (Sieck et al., J. Dent. Res. 69:1261–1265(1990)) for 2 weeks. A HAP-filled type IV composite-coated section was used as a control. After exposure, sections were removed from their holders and contact microradiographs were again made. A digital image analysis system (Bioquant System IV, R & M Biometrics Inc., Nashville, Tenn.) interfaced to a microscope (Leitz Ortholux, Germany) and a personal computer was used to obtain quantitative information on the mineral content of the enamel sections form the microradiographs (Chow et al., J. Res. Natl. Inst. Stand. Technol. 96:203–214(1991)). Results showed that tooth lesions coated with composite-containing $P_2O_7^{-4}$-stabilized ACP regained 22 to 35% of their lost mineral content after 2 weeks of immersion. Comparable treatment of lesions coated with HAP-containing composites regained less than 3% of their lost mineral. This latter finding shows that the substantial remineralization using ACP-filled composites was the result of migration and tooth deposition of mineral ions from the ACP and not from the immersion solution. The latter provided the water molecules necessary for the ion migration to take place.

EXAMPLE 8

Surface Modification of ACP by Silanization with 3-methacryloxypropyltrimethoxysilane Silanization, a procedure to surface modify glass and similar materials, was investigated as a method of surface modifying ACP. The primary rationale for silanizing ACP was to achieve a filler that would disperse better into monomer systems than untreated ACP. A compatible organic coating on ACP also may result in composites with higher loadings of well dispersed ACP and improved handling characteristics. Silanization also can enhance the physical, chemical, and mechanical properties of a composite.

To 1 gram of pyrophosphate stabilized ACP dispersed in 15 ml of dry cyclohexane was added 0.1 g of 3-methacryloxypropyltrimethoxysilane followed by 0.03 g of n-propylamine. The mixture was stirred magnetically at room temperature for 17 hours. The mixture was transferred to a flask and the solvent removed by a rotary evaporator by heating at 80°–90° C. at atmospheric pressure. The almost dry ACP powder was then heated for 1 hour at 90°–100° C. under a moderate vacuum (2–4 kilopascals) to yield the dry, silanized powder. The powder was triturated with fresh cyclohexane three times (3×10 ml) to remove unattached silane coating. The powder was vacuum filtered with the aid of a minimal amount of cyclohexane, air dried for 5 minutes and then dried at 65° C. for 30 minutes. Infrared analysis of the silanized powder indicated the presence of significant amounts of adsorbed and reacted 3-methacryloxypropyltrimethoxysilane. Evaporation of the cyclohexane washings and filtrates yielded only about 25 weight percent of the original silane agent.

The silanized ACP mixed with greater ease than untreated ACP with a one-to-one by weight BISGMA/TEGDMA monomer system (resin I of Table I) and permitted preparation of a composite paste containing 50 weight % ACP. Polymerization of this composite disk yielded a highly transparent composite disk, indicative of the superior dispersion of silanized ACP in composites compared to unsilanized ACP filler. Due to the presence of the silane coating, this type of composite when exposed to pH 7.4 buffered solution, gave 5 to 6 times higher release of $Ca^{2+}$ and phosphate ions than a similar untreated $P_2O_7$-stabilized ACP composite based on 1:1 BISGMA/TEGDMA (see FIG. 1).

What is claimed is:

1. A mineralizing composition for skeletal tissue comprising a mixture of
   an unsaturated monomer system, and
   a particulate mineralizing agent comprising amorphous calcium phosphate.

2. A mineralizing composition according to claim 1 wherein said unsaturated monomer system comprises at least one monomer which, upon polymerization, forms a polymer of sufficient permeability to permit slow diffusion of water and mineralizing agent to effect highly crystalline mineralization at a skeletal tissue interface.

3. A mineralizing composition according to claim 1 wherein said unsaturated monomer system includes at least one cross-linking agent.

4. A mineralizing composition according to claim 1 wherein said unsaturated monomer system includes at least one monomer, the homopolymer of which is hydrophilic.

5. A mineralizing composition according to claim 1 wherein said unsaturated monomer system includes at least one monomer, the homopolymer of which is hydrophilic and at least one cross-linking agent.

6. A mineralizing composition according to claim 2 wherein said at least one monomer includes a methacrylate moiety.

7. A mineralizing composition according to claim 4 wherein said at least one cross-linking agent comprises a methacrylate moiety.

8. A mineralizing composition according to claim 1 wherein said unsaturated monomer system includes a free-radical initiator.

9. A mineralizing composition according to claim 8 wherein said free-radical initiator is a photoinitiator.

10. A mineralizing composition according to claim 1 wherein said composition further includes a stabilizing agent.

11. A mineralizing composition according to claim 10 wherein said stabilizing agent includes Mg ions.

12. A mineralizing composition according to claim 10 wherein said stabilizing agent includes $CO_3$ ions.

13. A mineralizing composition according to claim 10 wherein said stabilizing agent includes $P_2O_7$ ions.

14. A mineralizing composition according to claim 1 wherein said unsaturated monomer system includes 2, 2 propane.

15. A mineralizing composition according to claim 1 wherein said unsaturated monomer system includes triethyleneglycol dimethacrylate.

16. A mineralizing composition according to claim 1 wherein said unsaturated monomer system includes 2-hydroxyethyl methacrylate.

17. A mineralizing composition according to claim 1 wherein said unsaturated monomer system includes zirconyl dimethacrylate.

18. A mineralizing composition according to claim 9 wherein said photoinitiator is camphorquinone.

19. A mineralizing composition according to claim 8 further including a polymerization accelerator.

20. A mineralizing composite for skeletal tissue comprising an inorganic particulate mineralizing agent which comprises amorphous calcium phosphate incorporated within a polymeric matrix.

21. A mineralizing composite according to claim 20 wherein said cross-linked polymeric matrix is of sufficient hydrophilicity to permit diffusion of water and ions therethrough.

22. A mineralizing composite according to claim 20 wherein said polymeric matrix is a cross-linked matrix.

23. A mineralizing composition according to claim 1 wherein the mineralizing filler is pretreated or treated in situ in the composite paste with an appropriate surface-active agent selected from the group consisting of silane, titanate, zirconate and aluminate class of compounds or mixtures thereof.

* * * * *